United States Patent [19]

Richter et al.

[11] 4,326,882
[45] Apr. 27, 1982

[54] TRICHLOROPHENOXY ALKANOIC ACID FREE OF CHLORINATED DIBENZO-P-DIOXINS

[75] Inventors: Sidney B. Richter, Akron; William S. Grove, Doylestown, both of Ohio

[73] Assignee: PPG Industries, Inc., Pittsburgh, Pa.

[21] Appl. No.: 33,349

[22] Filed: Apr. 26, 1979

Related U.S. Application Data

[63] Continuation-in-part of Ser. No. 937,645, Aug. 28, 1978.

[51] Int. Cl.³ ............... C07C 59/68; A01N 39/02; A01N 39/04
[52] U.S. Cl. .................. 562/472; 560/62; 560/63; 568/774; 568/778; 71/109; 71/110; 71/116; 71/118; 564/175
[58] Field of Search ............ 562/472; 560/62; 71/109, 110, 108; 260/559 B

[56] References Cited

U.S. PATENT DOCUMENTS

| | | | |
|---|---|---|---|
| 2,598,692 | 6/1952 | Henrich | 562/472 |
| 2,674,622 | 4/1954 | Gillies et al. | 562/472 |
| 2,717,907 | 9/1955 | Orwoll | 562/472 |
| 2,767,211 | 10/1956 | Cooper | 560/62 |
| 2,796,427 | 6/1957 | Huisman | 562/472 |
| 3,840,592 | 10/1974 | Sidwell | 560/62 |
| 3,840,593 | 10/1974 | Sidwell | 560/62 |
| 4,026,917 | 2/1978 | Stalling | 560/62 |

FOREIGN PATENT DOCUMENTS

| | | | |
|---|---|---|---|
| 559733 | 7/1958 | Canada | 560/62 |
| 592827 | 9/1947 | United Kingdom | 562/472 |
| 250154 | 1/1970 | U.S.S.R. | 562/472 |

OTHER PUBLICATIONS

Chemical Abst., vol. 54, 20940d, 1959.

*Primary Examiner*—Paul J. Killos
*Attorney, Agent, or Firm*—Edward J. Whitfield

[57] ABSTRACT

This invention provides as new compositions of matter 2,4,5-trichlorophenoxy acetic acid (2,4,5-T) and (2-2,4,5-trichlorophenoxy) propionic acid (Silvex) including the hydrolyzable salts, aliphatic esters and amides of these acids, which compositions are free of chlorinated dibenzo-p-dioxins.

8 Claims, No Drawings

TRICHLOROPHENOXY ALKANOIC ACID FREE OF CHLORINATED DIBENZO-P-DIOXINS

CROSS REFERENCE TO RELATED APPLICATION

This application is a continuation-in-part of application Ser. No. 937,645 filed Aug. 28, 1978 and relates to the compounds, 2,4,5-trichlorophenoxy acetic acid, 2-(2,4,5,-trichlorophenoxy) propionic acid including hydrolyzable salts, aliphatic esters and amides of these acids.

BACKGROUND OF THE INVENTION 2,4,5-trichlorophenoxy alkanoic acids, especially, 2,4,5-trichlorophenoxy acetic acid (2,4,5-T) and 2-(2,4,5-trichlorophenoxy) propionic acid (Silvex) and the salts, aliphatic esters and amides thereof are known to be particularly effective herbicides.

2,4,5-trichloropenoxyalkanoic acid, e.g., 2,4,5-T is typically prepared by condensing 2,4,5-trichlorophenol with haloalkanoic acid e.g., monochloroacetic acid in aqueous alkali metal hydroxide solution as described for example in U.S. Pat. No. 2,598,692. It is also known to prepare 2,4,5-trichlorophenoxyalkanoic acid, e.g., 2,4,5-T by chlorination of the sodium salt of 2,5-dichlorophenoxy acetic acid as described, for example in U.S. Pat. No. 2,717,907.

The use of both 2,4,5-T and Silvex has been severely curtailed by a recent order of the Environmental Protection Agency since each of these materials contain trace amounts of chlorinated dibenzo-p-dioxins, particularly 2,3,7,8-tetrachloradibenzo-p-dioxin (2,3,7,8-TCDD) which is produced as a by-product in the production of 2,4,5-T and Silvex.

2,3,7,8-TCDD is extremely toxic and there is evidence that it can be fatal to certain species of laboratory animals at levels as low as 0.6 microgram per kilogram of body weight.

Methods have been devised for treating 2,4,5 or Silvex to reduce their 2,3,7,8-TCDD content which methods are described, for example, in U.S. Pat. Nos. 4,026,917 and 3,840,593. In U.S. Pat. No. 4,026,917 dioxin is removed from 2,4,5-T by adsorption of the dioxin with coconut charcoal. This method is reported to reduce dioxin content of 2,4,5-T to less than 1 part per million. In U.S. Pat. No. 3,840,593 Silvex is subjected to fractional liquid-liquid extraction with a polar liquid solvent which reportedly reduces the dioxin content of the Silvex to typically less than 0.1 part per million. However, such treatment methods though removing a portion of the dioxin from 2,4,5-T or Silvex pose the problem of disposing of the dioxin-contaminated treating material, i.e. the charcoal in the case of U.S. Pat. No. 4,026,917 and the solvent in the case of U.S. Pat. No. 3,840,593. In other words such methods address only the symptoms rather than the cause. Moreover detectable amounts of dioxin remain in the treated 2,4,5-T and Silvex.

Prior to this invention, trichlorophenoxy alkanoic acids, e.g. 2,4,5-T, Silvex and hydrolyzable derivatives thereof free of detectable amounts of chlorinated dibenzo-p-dioxins, particularly 2,3,7,8-TCDD, have been unknown to the art, since previous processes have reputedly produced product containing varying quantities albeit in some cases small quantities of chlorinated dibenzo-p-dioxins.

For example, current manufacturing processes are believed capable of producing 2,4,5-T containing about 0.01 parts by weight of 2,3,7,8-TCDD per million parts by weight, 2,4,5-T. Although 10 parts per billion 2,3,7,8-TCDD in 2,3,4-T might ostensibly appear, for all practical purposes, negligible, due to the extreme toxic nature of 2,3,7,8-TCDD, material containing even such low levels is considered potentially hazardous.

SUMMARY OF THE INVENTION

This invention provides as new compositions of matter 2,4,5-trichlorophenoxy acetic acid (2,4,5-T) and 2-(2,4,5-trichlorophenoxy) propionic acid (Silvex) including the hydrolyzable salts, aliphatic esters and amides of these acids, which compositions are free of chlorinated dibenzo-p-dioxins.

DESCRIPTION OF THE INVENTION

In accordance with this invention the following compounds are provided:

2,4,5-trichlorophenoxy acetic acid (2,4,5-T) including hydrolyzable salts, aliphatic esters and amides thereof which acid as well as its hydrolyzable salts, aliphatic esters and amides are free of chlorinated dibenzo-p-dioxins; and 2-(2,4,5-trichlorophenoxy) propionic acid (Silvex) including hydrolyzable salts, aliphatic esters and amides thereof which acid as well as its hydrolyzable salts, aliphatic esters and amides are free of chlorinated dibenzo-p-dioxins.

With the exception of the salts, the dioxin-free compounds of this invention may be represented by the following formula:

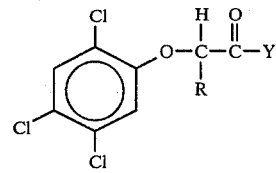

wherein R represents hydrogen or methyl; and Y represents hydroxy, or a hydrolyzable substituent selected from an aliphatic radical containing up to 20 carbon atoms, amide or mono-or di-substituted amide, the substituent of which contains up to 20 carbon atoms. When Y represents an aliphatic radical, the same is preferably an alkoxy or alkoxy-alkoxy group containing up to about 8 carbon atoms, some examples of which are, ethoxy, butoxy butoxy-ethoxy, iso-octoxy and the like. When Y represents a mono-or di-substituted amide, the substituent is preferably alkyl or alkoxy of up to about 8 carbon atoms. Preferably Y represents either hydroxy, or lower alkoxy, or alkoxy-alkoxy, i.e., the respective trichlorophenoxy alkanoic acid or ester thereof, which latter may be hydrolyzed to the free acid, which free acid may be readily converted to the salt-form by reaction with an organic or inorganic base.

The compounds of this invention are free of chlorinated dibenzo-p-dioxins, and especially 2,3,7,8-tetrachloro dibenzo-p-dioxin. By free of chlorinated dibenzo-p-dioxin is meant that said dioxins are incapable of detection by known analytic techniques. For example, in 2,4,5-T and 2,4,5-T ethyl ester of this invention 2,3,7,8-TCDD could not be detected at a level of less than 4 parts by weight 2,3,7,8-TCDD per trillion parts by weight of 2,4,5-T or 2,4,5-T ethyl ester.

The 2,4,5-trichlorophenoxy alkanoic acid esters of this invention are prepared by the liquid phase alkaline condensation of 2,5-dichlorophenol with an alpha haloalkanoic acid ester in an organic solvent under mild temperature conditions i.e., at a temperature of not more than about 60° C., and preferably not more than about 40° C. to produce 2,5-dichlorophenoxy alkanoic acid ester which is then chlorinated in the liquid phase, a chlorine atom replacing the hydrogen atom in the 4-position of the phenoxy substituent. The 2,4,5-trichlorophenoxy alkanoic acid ester may be hydrolyzed to the 2,4,5-trichlorophenoxy alkanoic acid which, if desired, may be converted to the salt form by reaction with an organic or inorganic base.

In like fashion, the 2,4,5-trichlorophenoxy acid amides of this invention are prepared by liquid phase alkaline condensation of 2,5-dichlorophenol with an alpha haloalkanoic acid amide in an organic solvent at a temperature of not more than about 60° C. preferably not more than about 40° C. to produce 2,5-dichlorophenoxy alkanoic acid amide which is chlorinated in the liquid phase to 2,4,5-trichlorophenoxy alkanoic acid amide. The 2,4,5-trichlorophenoxy acid amide may be hydrolyzed to 2,4,5-trichlorophenoxy alkanoic acid which in turn may be converted to the salt form by reaction with an organic or inorganic base.

The above described reaction sequence may be illustrated as follows:

I. Preparation of 2,5-dichlorophenoxy alkanoic acid ester or amide.

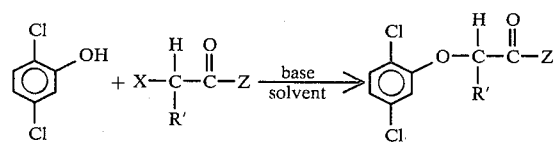

II. Preparation of 2,4,5-trichlorophenoxy alkanoic acid ester or amide.

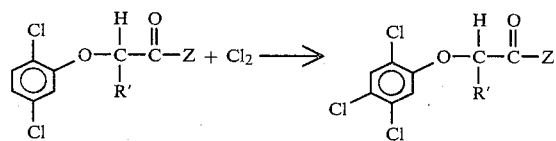

III. Preparation of 2,4,5-trichlorophenoxy alkanoic acid.

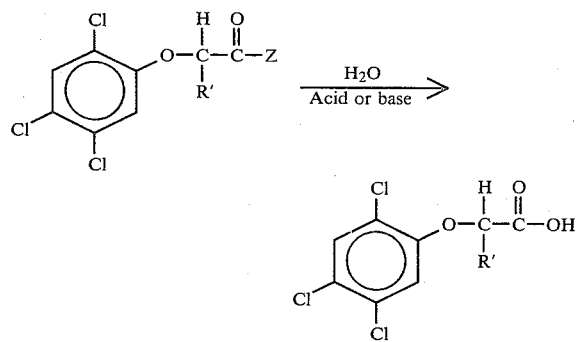

In the foregoing formulae, X is halogen, e.g. bromine, chlorine or iodine, R' is hydrogen or methyl; and Z is either a hydrolyzable aliphatic radical of up to 20 carbon atoms, preferably an alkoxy or alkoxy-alkoxy group of up to 8 carbon atoms, an amide or mono-or di-substituted amide, the substituent containing up to about 20 carbon atoms, preferably an alkyl or alkoxy group of up to about 8 carbon atoms.

It is believed that too high a temperature, too alkaline a reaction medium or a combination of both produce an environment conducive to the condensation of chlorinated phenols with each other to produce chlorinated dibenzo-p-dioxins. Consequently in reaction I, it is essential that the temperature not exceed about 60° C. preferably not more than about 40° C. It has been observed that reaction I proceeds favorably at ambient temperature, i.e. about 20° C. to 23° C. Although temperatures lower than 20° C. may be employed, i.e. about 0° C., too low a temperature will result in an unduly prolonged reaction time.

In reaction I, equimolar quantities of 2,5-dichlorophenol and the alpha haloalkanoic acid ester or amide and base are preferably used although to ensure complete reaction of the phenol group, up to about a ten percent molar excess of the alpha halo compound is typically used. A slight molar excess of base may be employed, i.e., up to about 5 percent, care being taken to avoid excess base much beyond a 5 percent molar excess. Both inorganic as well as organic bases may be used. Exemplary of suitable inorganic bases are the alkali and alkaline earth metal hydroxides, such as sodium hydroxide, potassium hydroxide and calcium hydroxide. Exemplary of organic bases are aliphatic amines such as methylamine, dimethylamine, trimethylamine, ethylamine, diethylamine, tetraethylamine, pyridine, or N, N-dimethylaniline. The alkali metal hydroxides are preferably used.

Reaction I is conducted in an anhydrous or aqueous organic solvent. Preferred solvents are alkyl alcohols such as ethanol, n-propanol, isoproponol, iso-butanol, n-butanol, and the like. When preparing 2,5-dichlorophenoxy-alkanoic acid ester, the alcohol used as a solvent preferably corresponds to the desired ester. For example, when ethyl-2,5-dichlorophenoxy acetate is prepared by condensing 2,5-dichlorophenol with, for example, ethyl bromoacetate the reaction is preferably conducted in an ethanol medium. Exemplary of other solvents that may be used as the medium for reaction I, are acetone, tetrahydrofuran, dimethyl formamide and dimenthylsulfoxide.

Chlorination of the 2,5-dichlorophenoxy alkanoic acid ester or amide (reaction II) is typically conducted in known fashion in a liquid solvent, e.g., carbon tetrachloride either in the absence of a catalyst or in the presence of a suitable catalyst, such as iodine, metallic iron or tin or ferric chloride.

Hydrolysis of the 2,4,5-trichlorophenoxy alkanoic acid ester or amide to the free acid may be conducted in known fashion by for example treating the amide or ester with an aqueous solution of alkali metal hydroxide or an aqueous solution of a mineral acid.

Conversion of the free acid to its corresponding metal salts or amine salts may be affected in known fashion by reacting the acid with an inorganic or organic base, such as those enumerated hereinabove in the discussion of reaction I.

The 2,5-dichlorophenol used as a starting material in the preparation of the compositions of this invention should be of as high a purity as possible and substantially free of 2,4-dichlorophenol and other chlorinated isomers. The 2,5-dichlorophenol should be at least 99 percent pure and preferably at least 99.5 percent pure.

The 2,5-dichlorophenol may be prepared by methods known to the art, such as, for example, alkaline hydrolysis of 1,2,4-trichlorobenzene. A particularly preferred method of preparing 2,5-dichlorophenol involves reacting the sulfate salt of 2,5-dichloroaniline with alkali metal nitrite, e.g., sodium nitrite, followed by hydrolysis of the diazonium salt.

The invention is further illustrated but it is not intended to be limited by the following example.

1. Preparation of 2,5-Dichlorophenol

To 400 ml of concentrated sulfuric acid in a 2-liter flask was added 145 grams (0.895 mole) of solid 2,5-dichloroaniline over a 5-minute period. Over the addition period the solution exothermically reached a temperature of 60° C. The sulfate salt solution of 2,5-dichloroaniline was cooled in an ice bath to about 5° C. and a solution of 65.6 grams (0.95 mole) of vacuum dried sodium nitrite in 400 ml concentrated sulfuric acid was added at such rate as to cause no exotherm. The mixture was stirred at 0° C. to 5° C. for about 30 minutes, was warmed to ambient temperature and stirred for an additional one hour. 450 ml of water was slowly added to the stirred mixture and the diluted mixture was steam distilled for about 15 minutes. An additional 450 ml of water was slowly added and the mixture steam distilled for about 75 minutes. The head temperature at the start of distillation was 145° C., the head temperature at the completion of distillation was 125° C., and the final pot temperature was 157° C. The distillate was transferred to a separatory funnel and extracted with 300 ml, 200 ml and 100 ml portions of methylene chloride. The extracts were combined and concentrated on a rotary evaporator at 55° C. and 40 mm $H_g$ to remove methylene chloride. 135 grams, corresponding to a 92 percent yield, of slightly orange-colored 2,5-dichlorophenol was thus obtained.

2. Preparation of Ethyl 2,5-Dichlorophenoxy Acetate

To a three-necked, 1000 ml flask provided with a mechanical stirrer and a reflux condenser was added 130.4 grams (0.8 mole) 2,5-dichlorophenol (prepared as described in step 1) dissolved in 300 ml absolute, i.e., anhydrous, ethanol. To the phenol solution was added, at ambient temperature, 32.4 grams (0.81 mole) sodium hydroxide dissolved in 300 ml absolute ethanol. The resulting mixture was stirred for 30 minutes and then 133.6 grams (0.8 mole) ethyl bromoacetate was added over a period of 15 minutes. The resulting mixture was stirred for about 30 hours at ambient, i.e., about 23° C., temperature. (A white precipitate, believed to be sodium bromide, was apparent after stirring for about 1 hour.) After completion of stirring the mixture was filtered and the filtrate was concentrated on a rotary evaporator at 55° C., 140 mm $H_g$ and a suspended solids containing liquid was obtained. Both the liquid and the solids were taken-up in 200 ml carbon tetrachloride and transferred to a separatory funnel. The mixture was washed twice with 50 ml portions of 1 N sodium hydroxide solution and once with 50 ml of water. After washing, the organic phase was separated, dried over magnesium sulphate, filtered and the filtrate concentrated on a rotary evaporator at 55° C., 140 mm $H_g$, a reddish-yellow liquid being obtained. The liquid was taken up in 150 ml of carbon tetrachloride, treated with 2 grams activated charcoal, filtered and the filtrate was concentrated on a rotary evaporator at 55° C., 140 mm $H_g$. 190 grams of a light yellow liquid corresponding to a 92 percent yield of ethyl-2,5-dichlorophenoxy acetate was thus obtained.

3. Preparation of Ethyl-2,4,5-Trichlorophenoxy Acetate

To a three-necked 1000 ml flask, provided with a reflux condenser, magnetic stirrer bar and a gas inlet tube, was added 148.8 grams (0.6 mole) of ethyl-2,5-dichlorophenoxy acetate (prepared as described in step 2) dissolved in 500 ml of carbon tetrachlroide, and 2.5 grams anhydrous ferric chloride. The mixture was stirred vigorously and chlorine gas was bubbled into the mixture at ambient, i.e., about 23° C., temperature for about 7 hours. The chlorinated mixture was then degassed with nitrogen, filtered, and the filtrate transferred to a separatory funnel. The filtrate was washed twice with 250 ml portions of 1 N hydrochloric acid and once with 250 ml of water. The organic phase was separated, dried over magnesium sulphate and concentrated on a rotary evaporator at 55° C., 140 mm $H_g$. A yellow oil was obtained which, upon cooling to ambient temperature, yielded 155 grams (90 percent yield) of crude, tan-colored crystalline ethyl-2,4,5-trichlorophenoxy acetate.

About 18 grams of the crude ethyl-2,4,5-trichlorophenoxy acetate was swirled with 15 ml of ethyl acetate and treated with 50 ml of ligroin (petroleum ether). Upon evaporation of the solvent, 11 grams of finely divided light yellow solid ethyl-2,4,5-trichlorophenoxy acetate was obtained.

4. Preparation of 2,4,5-Trichlorophenoxy Acetic acid

About 5.67 grams (0.02 mole) of ethyl-2,4,5-trichlorophenoxy acetate (prepared as described in Step 3) was treated with 3.2 grams (0.08 mole) of sodium hydroxide dissolved in 25 ml of water. The mixture was refluxed with constant stirring for 4 hours. After refluxing, the mixture was cooled to ambient temperature, diluted with 15 ml of water and carefully poured into 50 ml of concentrated hydrochloric acid, forming a white precipitate. The precipitate was separated by filtration and dried at 70° C. in a vacuum oven. The dried precipitate was recrystallized from a mixture of 30 volume percent ethyl acetae and 70 volume percent ligroin leaving a white, crystalline, solid of pure 2,4,5-trichlorophenoxy acetic acid (melting point 150° C. to 153° C.)

In both the ethyl-2,4,5-trichlorophenoxy acetate prepared in step 3 and the 2,4,5-trichlorophenoxy acetic acid prepared in step 4 no 2,3,7,8-tetrachloro-dibenzo-p-dioxin could be detected at a level of less than 4 parts by weight 2,3,7,8-TCDD per trillion parts of either ethyl-2,4,5-trichlorophenoxy acetate or 2,4,5-trichlorophenoxy acetic acid.

Although the invention has been described with reference to specific details of illustrative embodiments thereof, it is not intended that it be so limited unless as set forth in the appended claims.

We claim:

1. In a process for preparing 2,4,5-tri-chlorophenoxy alkanoic acid esters or amides by reacting in a liquid organic solvent and in the presence of an inorganic or organic base 2,5-dichlorophenol with at least an equimolar amount of alpha halo compound represented by the formula:

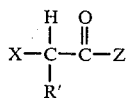

wherein

X is bromine, chlorine or iodine;

R' is hydrogen or methyl; and

Z is a hydrolyzable group selected from aliphatic radicals containing up to 20 carbon atoms or amide or mono- or di-substituted amide, the substituent containing up to about 20 carbon atoms, and chlorinating the reaction product in the liquid phase, the improvement wherein the reaction between 2,5-dichlorophenol and the alpha halo compound is conducted at a temperature of not more than 60° C. and in the presence of at least one mole but not more than a 5 percent molar excess of base per mole of 2,5-dichlorophenol, so as to obtain a pure product that is free of analytically detectable amounts of chlorinated dibenzo-p-dioxins.

2. The improvement of claim 1 wherein the base is an alkali metal hydroxide.

3. The improvement of claim 1 wherein the reaction temperature does not exceed about 40° C.

4. The improvement of claim 1 wherein Z is alkoxy or alkoxy-alkoxy containing up to 8 carbon atoms.

5. The improvement of claim 1 wherein Z is a mono- or di-substituted amide said substituent selected from alkyl or alkoxy of up to 8 carbon atoms.

6. The improvement of claim 1 wherein the reaction medium is anhydrous or aqueous aliphatic alcohol.

7. The improvement of claim 4 including the step of hydrolyzing the 2,4,5-trichlorophenoxy alkanoic acid ester or amide to produce 2,4,5-trichlorophenoxy alkanoic acid selected from 2,4,5-trichlorophenoxy acetic acid and 2-(2,4,5-trichlorophenoxy) propionic acid.

8. The improvement of claim 7 including the step of reacting the 2,4,5-trichlorophenoxy alkanoic acid with an organic or inorganic base to convert the 2,4,5-trichlorophenoxy alkanoic acid to the salt form.

* * * * *